US006827900B2

United States Patent
Thiem et al.

(10) Patent No.: US 6,827,900 B2
(45) Date of Patent: Dec. 7, 2004

(54) AUTOMATIC STAINER HAVING A HEATING STATION

(75) Inventors: Stefan Thiem, Heidelberg (DE); Charilaos Dalkidis, Oftersheim (DE)

(73) Assignee: Leica Microsystems Nussloch, GmbH, Nussloch (DE)

( * ) Notice: Subject to any disclaimer, the term of this patent is extended or adjusted under 35 U.S.C. 154(b) by 142 days.

(21) Appl. No.: 09/780,807

(22) Filed: Feb. 9, 2001

(65) Prior Publication Data

US 2001/0019703 A1 Sep. 6, 2001

(30) Foreign Application Priority Data

Feb. 11, 2000 (DE) .......................................... 100 06 084

(51) Int. Cl.[7] .................. G01N 21/00; G01N 31/00; G01N 15/06; B05C 19/02; B05D 3/00
(52) U.S. Cl. .................. 422/63; 67/68.1; 118/423; 427/2.11
(58) Field of Search .................. 422/63–65, 67, 422/99, 100, 68.1, 104; 118/423, 425; 427/2.11; 436/43, 46

(56) References Cited

U.S. PATENT DOCUMENTS

| | | | | | |
|---|---|---|---|---|---|
| 3,691,988 A | * | 9/1972 | Clarke | .......................... | 118/699 |
| 3,837,795 A | * | 9/1974 | Becker et al. | .............. | 118/423 |
| 3,976,028 A | * | 8/1976 | Howells et al. | ............. | 118/702 |
| 4,092,952 A | * | 6/1978 | Wilkie et al. | .................. | 118/58 |
| 4,353,856 A | * | 10/1982 | Muck et al. | ................. | 264/240 |
| 4,436,764 A | * | 3/1984 | Nakazima et al. | .......... | 118/423 |
| 4,651,671 A | * | 3/1987 | Pedersen | ..................... | 118/57 |
| 4,738,824 A | * | 4/1988 | Takeuchi | .................... | 118/425 |
| 4,911,098 A | * | 3/1990 | Tabata | ......................... | 118/423 |
| 5,573,727 A | * | 11/1996 | Keefe | .......................... | 422/63 |
| 5,588,202 A | * | 12/1996 | Ehlers et al. | ............... | 174/52.2 |
| 6,017,495 A | * | 1/2000 | Ljungmann | ................... | 422/65 |
| 6,058,788 A | * | 5/2000 | Thiem et al. | ................ | 422/101 |
| 6,080,363 A | * | 6/2000 | Takahashi et al. | ........... | 118/625 |
| 6,180,061 B1 | * | 1/2001 | Bogen et al. | ................. | 422/64 |
| 6,183,693 B1 | * | 2/2001 | Bogen et al. | ................. | 422/64 |
| 6,258,322 B1 | * | 7/2001 | Meikle | ......................... | 422/63 |
| 6,296,809 B1 | * | 10/2001 | Richards et al. | .............. | 422/64 |
| 6,387,326 B1 | * | 5/2002 | Edwards et al. | .............. | 422/63 |
| 6,436,348 B1 | * | 8/2002 | Ljungmann et al. | .......... | 422/63 |

FOREIGN PATENT DOCUMENTS

WO    WO 99/20995    4/1999

OTHER PUBLICATIONS

COT 20 Tissue Stainer, http://www.medite–histotechnic.com\COT20DE.htm.
Sakura Tissue–Tek SCA, Coverslipper Linear Stainer II.

* cited by examiner

Primary Examiner—Jill Warden
Assistant Examiner—Brian R. Gordon
(74) Attorney, Agent, or Firm—Hodgson Russ LLP

(57) ABSTRACT

An automatic stainer for staining specimens that are arranged on specimen slides and embedded in a medium, preferably in paraffin, is described. The automatic stainer has multiple reagent containers arranged one behind another for treating the specimens. During staining, the specimen slides pass successively through the reagent containers. There are transport baskets for receiving multiple specimen slides, multiple transport baskets being received simultaneously each in different reagent containers. A motorized transport mechanism, with a lifting device that lifts all the transport baskets simultaneously out of the respective reagent container and transports them on into the respective adjacent reagent container, is provided. A heating station for heating the specimens and melting the embedding medium is arranged in front of the row of reagent containers. The heating station has at least one melting container for simultaneously receiving multiple transport baskets.

5 Claims, 3 Drawing Sheets

AUTOMATIC STAINER HAVING A HEATING STATION

CROSS-REFERENCE TO RELATED APPLICATIONS

This application claims priority of a German patent application DE 100 06 084.6 filed Feb. 11, 2000 which is incorporated by reference herein.

FIELD OF THE INVENTION

The invention concerns an automatic stainer for staining specimens that are arranged on specimen slides and embedded in a medium, preferably in paraffin, in which multiple reagent containers arranged one behind another are provided for treating the specimens, and the specimen slides pass successively through the reagent containers; having a transport basket for receiving multiple specimen slides, such that multiple transport baskets can be received simultaneously each in different reagent containers; and having a motorized transport mechanism with a lifting device that lifts all the transport baskets simultaneously out of the respective reagent container and transports them on into the respective adjacent reagent container.

BACKGROUND OF THE INVENTION

The histological specimens provided for microscopic examination are placed onto specimen slides after being cut with a microtome. The specimen slide is then appropriately labeled and cataloged. To increase contrast for a subsequent microscopic examination, these specimens are then stained, making the structures in the cells or the tissues visible in differentiated fashion. In addition to various special stains, one standard staining process has become established in practical use. In this "hematoxylin-eosin" staining method, the specimens pass through different processing stages with xylene, alcohol, eosin, hematoxylin, acetic acid, and water. Various types of automatic stainers, which automatically convey the specimens to the respective processing stages, are used to stain the specimens.

Automatic stainers with a simplified transport mechanism and a high preparation throughput are offered by the company styled "medite" under the designation "COT 20," and by the company styled "Sakura" under the designation "Linear Slide Stainer II." Both automatic stainers operate on the principle of a continuously recirculating transport motion for the transport baskets in which the specimen slides with the specimens are located. During the transport motion, the transport baskets are transported, at constant cycling times, into the reagent containers arranged one behind another. Any necessary residence time for the specimens in the respective containers is achieved using multiple reagent containers arranged one behind another. The transport basket is suspended in a transport rail, and conveyed by the transport rail a specific distance to the next reagent container where it is lowered again. The transport rail travels beneath the support bracket of the transport basket back into its starting position. Another transport basket can now be placed onto the transport rail. Once a predefined time interval has elapsed, the transport rail simultaneously lifts up all the transport baskets present in the automatic stainer, and transports them into the next reagent containers.

Before the specimens (usually embedded in paraffin) can be subjected to treatment in an automatic stainer of this kind, the embedding medium (in this case paraffin) must be gently removed. Otherwise the risk exists that the staining solutions will not be able to penetrate into the tissue. For this reason, before treatment the specimen slides are heated in a separate oven until the paraffin present on the specimen slides has vaporized or melted.

The separate oven makes an additional manual process step necessary in this case. The risk also exists, when the heated specimen slides are being handled, that the operator may be burned and that hot specimen slides may be dropped upon removal.

BRIEF SUMMARY OF THE INVENTION

It is therefore the object of the present invention to further develop a known automatic stainer in such a way that no additional manual working steps are necessary in order to remove the embedding medium prior to staining of the specimen.

This object is achieved, according to the present invention, by the features recited herein.

The automatic stainer is characterized in that a heating station for heating the specimens and melting the embedding medium is arranged in front of the row of reagent containers and is integrated into the transport mechanism, and the heating station has at least one melting container for simultaneously receiving multiple transport baskets.

In an embodiment of the invention, the heating station has an oven housing which is equipped with a fan and an electric heating package. Instead of a fan, it is of course also possible to provide a fluid which is heated by the heating package.

An air distributor, which directs the heated air via an opening in the wall or the floor of the melting container onto the specimen slides, can be provided in the oven housing.

In a further embodiment of the invention, the temperature inside the heating station can be adjusted by way of a controller. If multiple melting containers arranged next to one another are present in the heating station, the temperature in each melting container can be adjusted separately by way of the controller.

The lifting device can be equipped with two transport rails, arranged parallel to one another, which are each equipped with a transport notch in the region of the reagent containers, and with a sawtooth profile in the region of the heating station. As a result, in the region of the reagent containers the transport baskets are transported on into the respective adjacent reagent container with one transport stroke, the transport baskets simultaneously traveling a shorter distance in the region of the heating station. The sawtooth profile is configured in such a way that the brackets of the transport baskets, when lifted, slide down on the flanks of the profile and are entrained only by the shoulder.

In an embodiment of the invention, two support rails equipped with grooves are arranged in the region of the heating station, parallel to the transport rails, as a support for the brackets of the transport baskets.

The spacing between adjacent grooves can be half as great as the spacing between the individual reagent containers arranged one behind another.

In the case of the sawtooth profile, the slope of the flanks and their spacing from one another can be such that in the region of the heating station, each transport basket is conveyed into the adjacent groove with one transport stroke.

Advantageously, the heating station is configured as a separate and retrofittable module.

BRIEF DESCRIPTION OF THE DRAWINGS

The invention will be explained in more detail with reference to an exemplary embodiment, with the aid of the schematic drawings, in which.

DETAILED DESCRIPTION OF THE INVENTION

Figure 1:
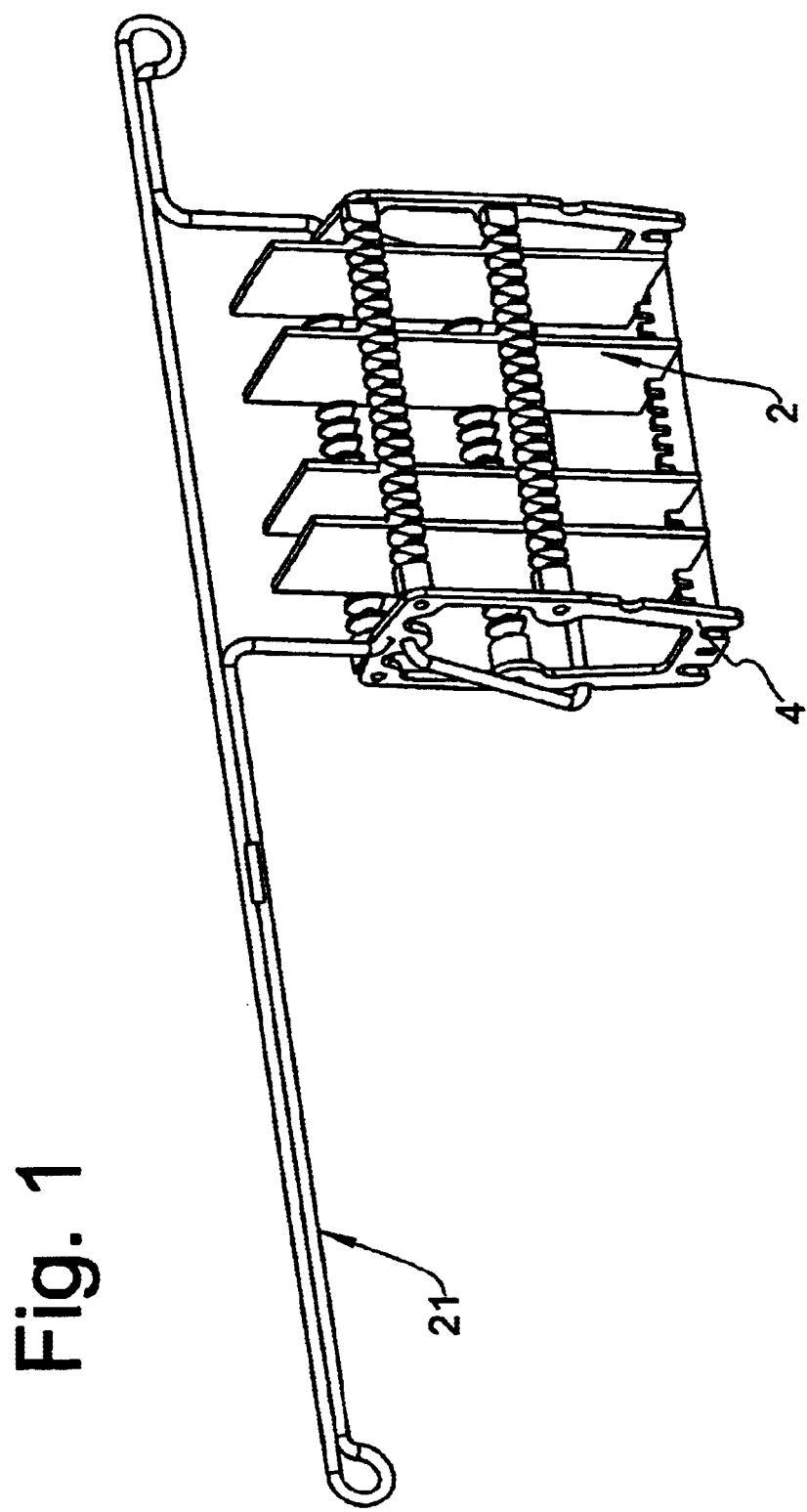
FIG. 1 shows a view of a transport basket with specimen slides.

FIG. 1 shows a transport basket 4 with four specimen slides 2 in place, as ordinarily used for transport in the automatic stainer described below. Mounted detachably on transport basket 4 is a transport bracket 21 with which transport basket 4 is suspended in the transport mechanism of the automatic stainer. Transport basket 4 and the transport bracket are in this case, advantageously, made of stainless steel.

Figure 2:
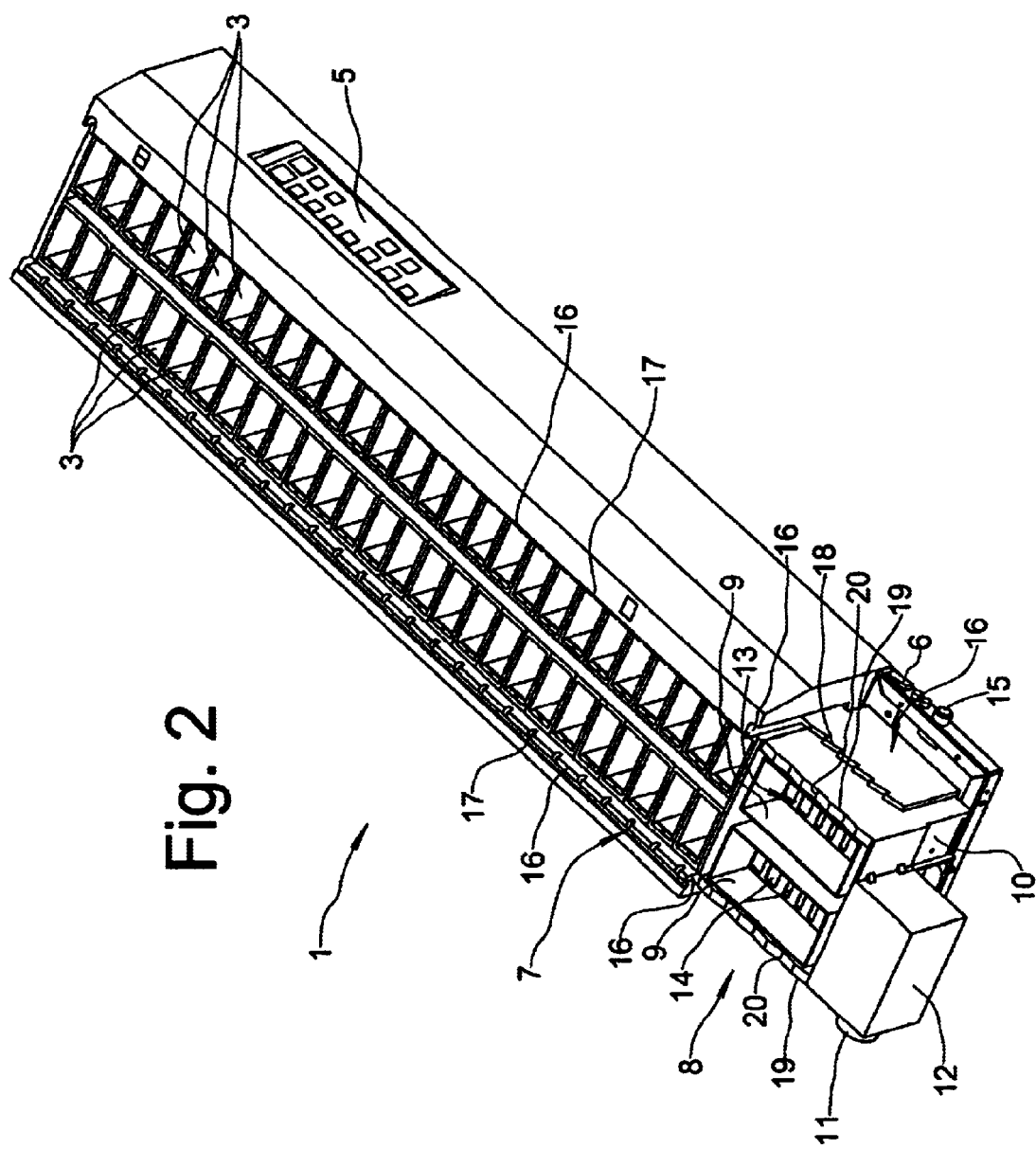
FIG. 2 shows a view of the automatic stainer with the heating station attached.

FIG. 2 shows an automatic stainer 1 having a control panel 5 and two rows of multiple reagent containers 3 arranged one behind another. A heating station 8, with one melting container 9 for each row of reagent containers, is arranged at the left end of automatic stainer 1. Transport baskets 4 (FIG. 1) with specimen slides 2 (FIG. 1) arranged therein are suspended by way of transport brackets 21 (FIG. 1) in melting containers 9. The motorized transport mechanism has a lifting device 7 with which transport baskets 4 (FIG. 1) are moved stepwise from left to right. Lifting device 7 has for that purpose respective transport rails 16, arranged one on the right-hand row of reagent containers and one on the left, having transport notches 17. The two rails 16 are immovably joined to one another. In the region of heating station 8, the transport notches in transport rails 16 are configured as a sawtooth profile 18. In heating station 8, a support rail 19 is arranged parallel to each transport rail 16. Grooves 20 for receiving bracket 21 (FIG. 1) on transport basket 4 (FIG. 1) are provided in these support rails 19.

In the region of reagent containers 3, baskets 4 are transported on, in the context of the transport motion, into containers 3 arranged one behind another. In that context, transport basket 4 is lifted completely out of reagent container 3 by way of transport notches 17 in transport rail 16 of lifting device 7, then transported horizontally to the next reagent container 3 and there lowered again. Transport rail 16 is lowered by lifting device 7 until transport bracket 16 leaves transport notches 17 and is supported on the frame of reagent container 3 or the frame of automatic stainer 1. Lifting device 7 is now disengaged, and travels back, beneath transport bracket 21 of transport basket 4, into its starting position. After a predefined cycle time has elapsed, lifting device 7 simultaneously lifts all transport baskets 4 and transports them into the next reagent container 3.

Baskets 4 are transported in equivalent fashion in the region of heating station 8. Here, however, the transport notches in transport rails 16 are configured as a sawtooth profile 18. Brackets 21 of transport baskets 4 therefore slide down on the flanks of sawtooth profile 18 when transport rails 16 are lifted, and are entrained only by the shoulders on sawtooth profile 18. Brackets 21 of transport baskets 4 are then set down into the next groove 20 of support rail 19. The slope of the flanks of sawtooth profile 18 is such that with each transport step, transport basket 4 travels approximately half the distance traveled by transport basket 4 in the region of reagent containers 3. The spacing of grooves 20 present in support rails 19 is also adapted to this shorter distance. The result is that in the region of heating station 8, transport baskets follow one another more closely and the space required for transport baskets 4 is thus minimized.

Figure 3:
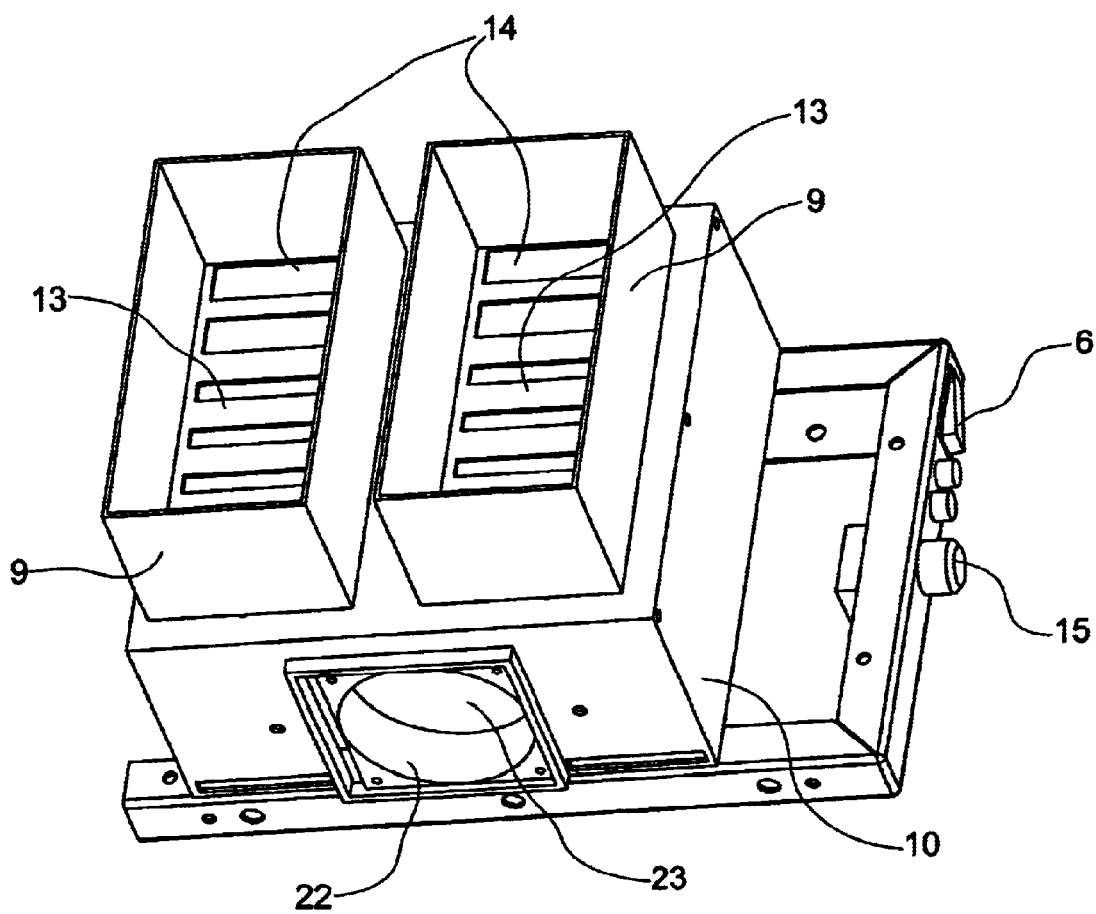
FIG. 3 shows a view of the oven housing with heating package.

Heating station 8 has an oven housing 10 having a fan 22 and an electrically operating heating package 23 (FIG. 3). Air is drawn in from below by fan 22 and heated by heating package 23. The heated air is then directed from below, via an air distributor 13, into melting containers 9. For that purpose, several openings 14 in the walls and/or floor of melting containers 9 are associated with air distributor 13. The air emerging from the top of melting containers 9 is drawn into a fan housing 12 by a fan, and conveyed via a connector tube 11 to an air discharge system (not depicted). It has proven to be advantageous to draw off the hot air in this fashion, since otherwise the entire unit, along with the reagent containers, would heat up. The volatile reagents, for example xylene or alcohol, would evaporate without being used.

Heating station 8 is equipped with a controller 15 in order to adjust the temperature. If multiple melting containers 9 are used in heating station 8, the temperature in each container 9 can be adjusted separately and independently by way of controller 15. Heating package 23 of the heating station can be switched on and off using main switch 6.

Specimen slides 2 with the specimen embedded in paraffin are heated by the hot air. The paraffin melts and partially vaporizes from specimen slides 2. At the end of melting container 9, specimen slide 2 with the specimen has been heated so that any remaining paraffin still present can very easily be dissolved away. This is accomplished by the fact that transport basket 4 is lifted by lifting device 7 into the first reagent container 3. The first reagent container 3 is usually filled with xylene, a very good solvent for paraffin.

The heating station can be configured as a retrofittable module, and adapted to the various automatic stainers. All that is necessary for that purpose is an adapter which extends the transport rails of the automatic stainer and has a corresponding sawtooth profile. The heating station can of course be used not only for specimens embedded in paraffin, but also in cases where the preparation is embedded, for example, in a suitable medium such as plastic.

FIG. 3 shows a schematic depiction of oven housing 10 with fan 22 and heating package 23. Air is drawn in by fan 22, heated by heating package 23, and delivered through openings 14 to melting containers 9.

In this exemplary embodiment, the heating station is described as a hot-air heating system. It is understood that this heating system can also be implemented with a water bath or a bath having a suitable fluid.

PARTS LIST

1 Automatic stainer
2 Specimen slide
3 Reagent container
4 Transport basket
5 Control panel
6 Main switch
7 Lifting device
8 Heating station
9 Melting container
10 Oven housing
11 Connector tube
12 Fan housing
13 Air distributor
14 Openings
15 Controller
16 Transport rails
17 Transport notches
18 Sawtooth profile

19 Support rails
20 Grooves in 19
21 Transport brackets
22 Fan
23 Heating package

What is claimed is:

1. In an automatic stainer for staining specimens that are arranged on specimen slides and embedded in a medium, said stainer comprising a plurality of reagent containers arranged one after another to successively receive said specimen slides for treating said specimens, a plurality of transport baskets each carrying one or more of said specimen slides such that said plurality of transport baskets can be received simultaneously each in a different one of said plurality of reagent containers, a motorized transport mechanism having a lifting device for simultaneously lifting said plurality of transport baskets out of said reagent containers and transporting said plurality of transport baskets into successive reagent containers, the improvement comprising:

a heating station arranged before said plurality of reagent containers for heating said specimen slides and melting said embedding medium, said heating station having at least two melting containers each for simultaneously receiving more than one of said plurality of transport baskets, said at least two melting containers arranged next to one another, and wherein said heating station further has a controller for adjusting the temperature in said at least two melting chambers, and the temperature in each of said two melting containers can be adjusted separately by way of said controller.

2. In an automatic stainer for staining specimens that are arranged on specimen slides and embedded in a medium, said stainer comprising a plurality of reagent containers arranged one after another to successively receive said specimen slides for treating said specimens, a plurality of transport baskets each carrying one or more of said specimen slides such that said plurality of transport baskets can be received simultaneously each in a different one of said plurality of reagent containers, a motorized transport mechanism having a lifting device for simultaneously lifting said plurality of transport baskets out of said reagent containers and transporting said plurality of transport baskets into successive reagent containers, the improvement comprising:

a heating station arranged before said plurality of reagent containers for heating said specimen slides and melting said embedding medium, said heating station having at least one melting container for simultaneously receiving more than one of said plurality of transport baskets, the improvement characterized in that said lifting device comprises two transport rails, arranged parallel to one another, which are each equipped with a transport notch in a region of said plurality of reagent containers and with a sawtooth profile in a region of said heating station, whereby in said region of said plurality of reagent containers said plurality of transport baskets is transported into the next respective reagent containers with one transport stroke, and in said region of said heating station said plurality of transport baskets travel a shorter distance with the same transport stroke.

3. The improvement as defined in claim 2, wherein said heating station further comprises two support rails parallel to said transport rails, each of said support rails having a plurality of spaced grooves for supporting one of said plurality of transport baskets while said transport basket is received by said melting container.

4. The improvement as defined in claim 3, wherein the spacing between adjacent grooves of said support rails is half as great as the spacing between successively adjacent reagent containers.

5. The improvement as defined in claim 3, wherein said sawtooth profile of said transport rails is dimensioned such that in the region of said heating station each said transport basket is conveyed into the next adjacent groove of said support rails with one transport stroke.

\* \* \* \* \*